Figure 1:
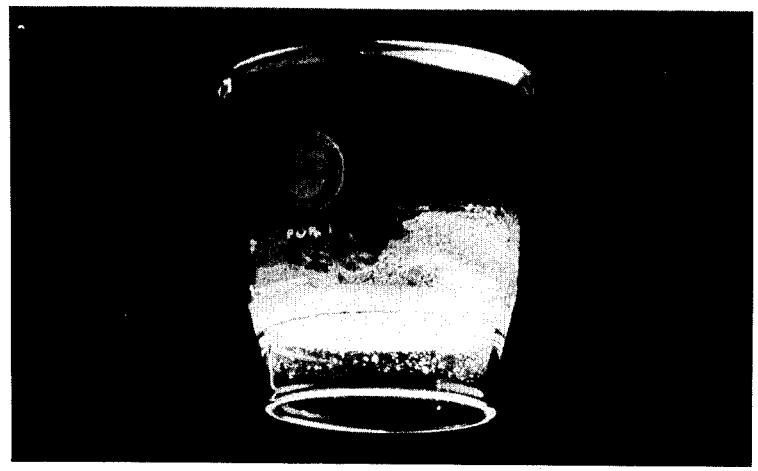
Figure 2:
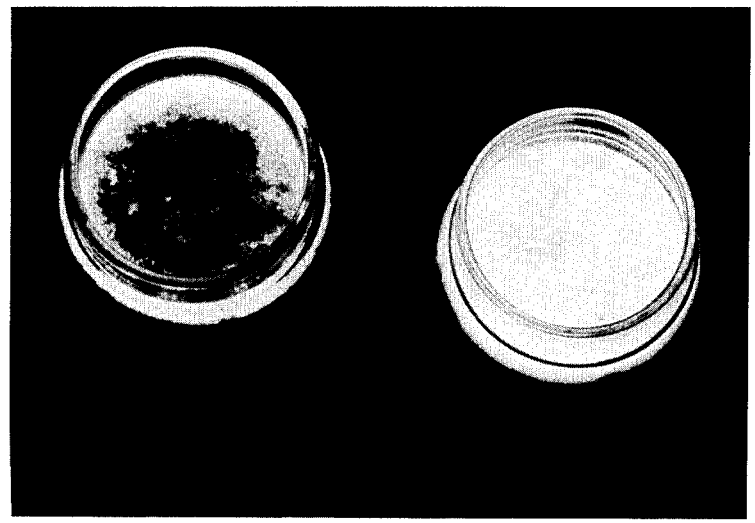

United States Patent [19]

Cacioli et al.

[11] Patent Number: 4,873,082
[45] Date of Patent: Oct. 10, 1989

[54] MULTI-LAYER BIRD REPELLANT COATING COMPOSITION

[75] Inventors: Paul Cacioli, Reservoir; Roger Snow, Sandringham, both of Australia

[73] Assignee: International Contamination Control Industries Pty Ltd., Victoria, Australia

[21] Appl. No.: 7,723

[22] Filed: Jan. 28, 1987

Related U.S. Application Data

[63] Continuation-in-part of Ser. No. 885,812, Jul. 15, 1986, which is a continuation of Ser. No. 620,944, Jun. 14, 1984, abandoned.

[30] Foreign Application Priority Data

Jan. 29, 1986 [AU] Australia .............................. PH4368

[51] Int. Cl.$^4$ ......................... A01N 27/00; A01N 25/04
[52] U.S. Cl. ...................................... 424/83; 514/918; 514/944
[58] Field of Search .................. 424/78, 83, DIG. 10; 514/918, 919, 920

[56] References Cited

U.S. PATENT DOCUMENTS

| | | | |
|---|---|---|---|
| 3,378,439 | 4/1968 | Reinert et al. | 167/46 |
| 3,496,278 | 2/1970 | Kohn et al. | 424/355 |
| 3,694,543 | 9/1972 | Needham et al. | 424/30 |
| 3,734,875 | 5/1973 | Sekuler | 260/31.2 R |
| 4,395,445 | 7/1983 | Gebauer | 428/422 |
| 4,499,143 | 2/1985 | Panush | 428/336 |

FOREIGN PATENT DOCUMENTS

| | | | |
|---|---|---|---|
| 705016 | 3/1965 | Canada | 167/28 |
| 487582 | 4/1970 | Switzerland . | |

OTHER PUBLICATIONS

Clauser, Henry; *Encyclopedia/Handbook Materials, Parts, and Finishes;* Technomic Publishing Inc., pp. 370–371.

Hyvis polybutenes, BP Chemicals Ltd., Dec. 1980.

Gelants for Organic and Water-Based Systems, Tixogen VP, Tixogel VZ, Tixogel WM, United Catalyst, Inc., 1981.

*Primary Examiner*—Mary C. Lee
*Assistant Examiner*—Mary Sue Howard
*Attorney, Agent, or Firm*—Merchant, Gould, Smith, Edell, Welter & Schmidt

[57] ABSTRACT

A multi-layer bird repellant coating for a substrate is provided which comprises:
(i) at least one bird repellant bead or strip formed from a bird repellant gel composition including:
 (a) about 75 to 98% by weight based on the total weight of the gel composition of at least one butene polymer or copolymer;
 (b) about 1 to 7% by weight based on the total weight of the gel composition of a clay-based thickening agent; and
 (c) about 1 to 3% by weight based on the total weight of the gel composition of a polar organic swelling agent;
said bird repellant bead or strip having sufficient tackiness to repel birds but not to substantially retard the birds and having sufficient viscosity to minimize the flattening of bead or strip; and
(ii) a protective coating layer, on said bird repellant bead or strip, formed from a protective coating composition including:
 (a) an effective amount of a polymeric component, which polymeric component includes at least one vinyl aromatic polymer or copolymer,
 (b) an effective amount of a solvent or emulsifier for the polymeric component;
the protective coating layer being sufficiently brittle so that the surface thereof is broken, in use, on contact with a bird.

9 Claims, 1 Drawing Sheet

MULTI-LAYER BIRD REPELLANT COATING COMPOSITION

CROSS-REFERENCE TO RELATED APPLICATIONS

This application is a continuation-in-part of application Ser. No. 885,812 filed July 15, 1986, which is in turn a continuation of application Serial No. 620,944 filed June 15, 1984, abandoned.

FIELD OF THE INVENTION

The present invention relates to a bird repellant coating for a substrate.

BACKGROUND OF THE INVENTION

In the prior art, bird repellant coatings are formed with a tacky consistency which is coated on at least a part of a surface to be protected. Contact with the tacky coating repels the birds. However, bird repellant compositions known in the prior art have been deficient in a number of aspects. While the coating should have a tacky consistency, if it is too tacky, it will pick up dust, leaves and the like quickly and be rendered inefficient very quickly. Moreover, birds may become stuck on the surface.

In applicant's Australian Patent Application No. 27487/84, there was described a bird repellant composition including a butene polymer or copolymer component and a thickening agent therefor. This bird repellant composition, which could be dispensed in a gel or bead form from a cartridge, provided some improvement over the prior art. However, difficulties remained as the bird repellant composition was still susceptible to being rendered ineffective by pick-up of dust, leaves, etc. Moreover, the bird repellant composition was susceptible to darkening in color.

Moreover, the polybutene-based bird repellant composition had a tendency to seep into certain porous surfaces to be protected. This had the dual disadvantages that it was wasteful and that the bird repellant composition was extremely difficult to remove from the surface when its useful life had ended. Accordingly, it is an object of the present invention to overcome, or at least alleviate, one or more of the difficulties related to the prior art.

SUMMARY OF THE INVENTION

Accordingly, in a first aspect, the present invention provides a multi-layer bird repellant coating composition for a substrate comprising:
(i) at least one bird repellant bead or strip formed from a bird repellant gel composition including:
  (a) approximately 75 to 98% by weight based on the total weight of the gel composition of at least one butene polymer or copolymer.
  (b) approximately 1 to 7% by weight based on the total weight of the gel composition of a clay-based thickening agent; and
  (c) approximately 1 to 3% by weight based on the total weight of the gel composition of a polar organic swelling agent;
said bird repellant bead or strip having sufficient tackiness to repel birds but not to substantially retard the birds and with sufficient viscosity to minimize the flattening of bead or strip; and (ii) a protective coating layer on said bird repellant bead or strip, formed by the application to the bead or strip of a coating composition comprising:
  (a) an effective amount of a polymeric component which polymeric component includes at least one vinyl aromatic polymer or copolymer,
  (b) an effective amount of a solvent or emulsifier for the polymeric component;
the protective coating layer being sufficiently brittle that the surface thereof is broken, in use, on contact with a bird.

The at least one bird repellant bead or strip may be applied to the substrate.

The bird repellant layer (i) and protective coating layer (ii) may be present in any suitable relative amounts. The weight ratio of bird repellant layer (i) to protective coating layer (ii) may range from approximately 40:1 to approximately 15:1, preferably 19:1.

The polymeric component (a) is present in amounts of from approximately 75 to 98% by weight of the bird repellant gel composition. The polymeric component may be present in amounts of from approximately 92.5 to 97.5% by weight of total gel composition, preferably 93% by weight.

The polymeric component includes at least one butene polymer or butene copolymer. The at least one butene polymer may comprise a major amount of the polymeric composition. In a preferred form, the at least one butene polymer may comprise substantially all the polymeric component. The polymeric component may further include other polymers or copolymers. The polymers may be selected to adjust the tackiness or viscosity as desired. These polymers may preferably be present in minor amounts. Preferably, the butene polymer component comprises approximately 75 to 100% by weight of the polymeric component. The polymers may be selected from addition polymers, e.g., rubbery polymers such as isobutene polymers and acrylic-butene copolymers.

The polymeric component may include preferably a high molecular weight butene polymer component and a low molecular weight butene polymer. Butene polymers, or "polybutenes" are polymers consisting essentially of polymerized isobutene. The components may be in the form of a blend. The high molecular weight butene polymer and low molecular weight butene polymer may be present in any suitable relative amounts which will allow for the creation of the desired degree of tackiness in order to repel various birds but with a high enough viscosity to minimize the flattening of the gel over an extended period. It will be understood that as the gel flattens, the contamination thereof will increase and the efficiency of the composition as a repellant will accordingly decrease.

The at least one butene polymer may be a polybutene. The polybutene may be of the type sold under the trade designation HYVIS®. These are synthetic hydrocarbon polymers manufactured by polymerization of olefins comprising isobutene. The polymers are long chain hydrophobic molecules with methyl group side chains. The polybutene sold under the designation HYVIS® 10 and available from B. P. Australia Ltd. (Melbourne, Australia) is particularly preferred as the low molecular weight component. HYVIS® 10 has a molecular weight (MW) of approximately 900 to 1000. The polybutene polymer sold under the trade designation HYVIS® 30 may be used as the high molecular weight component. HYVIS® 30 has a molecular weight (MW) of approximately 1300 to 1500. Alternative polybutene which may be used include those sold under the trade designation Indopol ® and available from Amoco Chemicals, U.S.A. See Canadian Patent No. 705,016, the disclosure of which is incorporated by reference herein. The low molecular weight and high molecular weight butene polymers may be present in a weight ratio of approximately 1:1.

As an alternative that will be discussed below, the bird repellant composition may be manufactured utilizing the low molecular weight polymer only. If desired, the high molecular weight polymer component may be added at the end of the manufacturing process.

The clay-based thickening agent (b) of the bird repellant gel composition may be a hydrophobic thickening agent. An organophilic clay may be used. A thickening agent of the type sold under the trade designation TIXOGEL ® may be used. The TIXOGEL ® VP thickening agent available from the United Catalysts Inc., Louisville, Ky., is particularly preferred. TIXOGEL ® is a proprietary clay-based material containing montomorillinite and aluminum hydrosilicate particles bonded to suborganic radicals, such as fatty quaternary ammonium ions. The structure of TIXOGEL ® VP and VZ is depicted in Gelants For Organics and Water-Based Systems, United Catalysts Inc. Technical Bulletin (9181). The clay-based material is solubilized in an organic medium. Other clay-based thickening agents which have been found to be suitable include those sold under the trade designations:

Claytone ® 34, available from Kaolin Australia Sales Pty. Ltd., Melbourne, Australia;

Bentone ® 34, available from Hardie Trading Pty. Ltd., Sydney, Australia; and

Godaclay ® 34, available from Goda Chemical Group Pty. Ltd., Melbourne, Australia; and Veegum ®, available from Vanderbilt Minerals, Murray, Ky., U.S.A.

The thickening agent may be present in a suitable amount which will provide the bird repellant composition with the requisite viscosity for use as a gel or bead composition. The thickening agent may be present in amounts of from 2 to 7% by weight, preferably 2.5 to 5% by weight based on the weight of the total bird repellant gel composition. The thickening agent may be present in an amount of approximately 4 to 5% by weight based on the total amount of butene polymer.

The polar organic swelling agent may be selected from polar organic solvents such as alcohols, for example, methanol and ($C_2$–$C_4$) alkanols; and ketones, for example, acetone and methylethyl ketone; and mixtures thereof. The swelling agent may be present in amounts of from 30 to 50% by weight based on the total weight of thickener and swelling agent. The swelling agent may be present in amounts of approximately 40% by weight based on the total amount of thickening agent in the bird repellant composition. The swelling agent may be present in amounts of from approximately 1 to 3%, preferably 25 by weight based on the weight of the total bird repellant gel composition.

A particularly preferred bird repellant gel composition according to the present invention includes a high molecular weight butene polymer and a low molecular weight butene polymer in approximately equal amounts. The total butene polymer content of the composition comprises 93% of the bird repellent gel composition. The other inert ingredients in the composition comprise the remaining 7% of the bird repellant gel composition. The bird repellant gel composition according to the present invention may further include other compounding ingredients. For example, pesticides, fillers, extenders, colorants and other compounding ingredients may be included.

The polymeric component (a) of the protective coating composition (ii) may be selected to provide a protective coating layer which is resistant to contamination with dust, leaves and the like. The polymeric component (a) may be selected to be sufficiently brittle so that the surface of the protective coating layer will be broken on contact with a bird. It will be understood from the above that the protective coating layer may be a very thin layer. A layer of approximately 100 micron to approximately ½ millimeter may be used.

The polymeric component (a) of the protective coating layer composition (ii) may be present in a minor amount in the protective coating composition. The polymeric component may be present in amounts from approximately 2 to 40% weight per volume based on the volume of emulsifier or solvent in the protective coating composition. Preferably, the polymeric component is present in amounts of from approximately 2 to 20 grams per 100 milliliters of the solvent or emulsifier.

The polymeric component may include at least one vinyl aromatic polymer or copolymer. The at least one vinyl aromatic polymer may comprise a major amount of the polymeric component of the protective coating composition. The polymeric component should be selected to be compatible with the polybutene polymer of the bird repellant gel composition. For this reason, acrylic polymers such as polymethyl methacrylate are not suitable for use in the protective coating layer according to the present invention. The polymeric component should provide a protective coating layer which is sufficient brittle to be broken by contact with a bird or other animal.

The vinyl aromatic polymer or copolymer may be selected from those formed from strene monomers, vinyl toluene monomers and derivatives thereof. Minor amounts of other addition monomers may be used. Minor amounts of acrylic and methacrylic monomers may be included.

A styrene polymer or copolymer is preferred. A crystalline styrene polymer is preferred. A styrene polymer having a weight average molecular weight of the order of approximately 200,000 to 500,000 may be used. A styrene polymer of the type sold under the trade designation LUSTREX ® LF555, HH101A or HH103 have been found to be suitable. The LUXTREX ® polymers are available from Monsanto Chemicals (Melbourne, Australia).

The solvents which may be used may be selected from dichloromethane, toluene, ethylacetate, tetrahydrofuran, cyclohexane, benzene, dioxane, methylethylketone, butyl acetate and lower chlorinated aliphatic hydrocarbons. The solvent may be selected from those which do not dissolve the polybutene polymer of the bird repellant gel composition. The solvents may be selected to provide a reasonable drying time. The solvents dichloromethane and ethylacetate are preferred. The solvents may be present in amounts of from approximately 60 to 98% volume to volume based on the total volume of the protective coating composition.

In a preferred aspect of the present invention, the multi-layer bird repellant coating composition further comprises:

(iii) a primer layer on the substrate formed from a primer composition including,
  (a) an effective amount of polymeric primer component which primer component includes at least on vinyl aromatic polymer, and
  (b) an effective amount of a solvent or emulsifier for the polymeric primer coating composition.

The primer composition may be the same as, or similar to, the protective coating composition of the bird repellant multi-layer coating.

In a further aspect of the present invention, there is provided a multi-layer repellant coating kit including:
(a) a bird repellant gel composition as described above in a suitable container, and
(b) a separately-packaged protective coating composition as described above in a suitable container.

The bird repellant gel composition (a) may be provided in a cartridge form for delivery in the form of a bead onto the substrate to be coated. The protective coating composition (b) may be provided in any suitable form. Any suitable vessel may be used, such as a tin or can. Alternatively, the protective coating composition may be provided in an aerosol form.

The bird repellant multi-layer coating kit may further include:
(c) a separately-packaged primer composition as described above in a suitable container.

The primer composition may be provided in a similar form to the protective coating composition.

In a still further aspect of the present invention, there is provided a method for preparing a bird repellant multi-layer coating on a substrate which method comprises:
(i) providing a substrate;
(ii) coating at least a portion of the substrate with at least one bird repellant bead or strip formed from a bird repellant gel composition as described above; and
(iii) coating the bead or strip with a protective coating layer formed from a protective coating composition as described above.

The method of preparing a bird repellant multi-layer coating may further comprise:
(iii) drying the at least one repellant bead or strip, prior to coating it with the protective coating layer.

It will be understood that, depending on weather conditions, the drying step may require the bead or strip to remain uncoated for approximately 1 to 24 hours.

The method of preparing a bird repellant multi-layer coating according to the present invention may further comprise, prior to step (ii), the preliminary step of
(ia) coating the substrate with a primer layer formed from a primer composition as described above.

The present invention will now be more fully described with reference to the accompanying examples. It should be understood, however, that the description following is illustrative only and should not be taken in any way as a restriction on the generality of the invention described above.

| Bird Repellant Gel Composition | |
|---|---|
| Component | % by weight |
| Polybutene (MW 900–1000) | 46.5 |
| Polybutene (MW 1300–1500) | 46.5 |
| Thickening Agent (TIXOGEL ® VP) | 5.0 |
| Swelling Agent (methylethyl ketone) | 2.0 |
| Protective Coating Composition | |
| Component | Amount |
| Polystyrene (LUXTREX ® HF555) | 20 grams |
| Dichloromethane | 1 liter |

One liter of dichloromethane was placed in a suitable mixing vat, 20 grams of polystyrene in pellet form was added slowly to the solvent and stirring continued until all of the styrene had dissolved.

Multi-Layer Coating

The bird repellant gel composition as described above was prepared in a gel as described in Australian Patent Application No. 27487/84 (U.S. application Ser. No. 620,944), the disclosures of which are incorporated by reference herein, for utilization in a cartridge delivery form. A bead of the bird repellant gel was laid down upon a section of a substrate; in this case, the roof of a building.

The protective coating composition prepared as described above was placed in a reservoir of an industrial spray gun. The protective coating layer was then sprayed over the surface of the bird repellant gel. A surface coating of approximately 0.5 millimeter thick of the polystyrene was thus formed. A solid coating formed in approximately one minute. The coating tool approximately two hours to fully dry.

The protected bird repellant gel was then monitored for three days at which time it was noted that birds landing on the surface easily broke through the protective layer and were repelled by the tackiness of the bird repellant gel. However, the movement of the birds was not substantially retarded, in that they did not become stuck to the gel and could resume flight.

In areas where there had not been contact with birds, deterioration due to build-up of dust, leaves and the like upon the surface of the bead was substantially diminished.

EXAMPLE 2

| Bird Repellant Gel Composition | |
|---|---|
| Component | % by weight |
| Polybutene (MW 900–1000) | 46.5 |
| Polybutene (MW 1300–1500) | 46.5 |
| Thickening Agent (TIXOGEL ® VP) | 5.0 |
| Swelling Agent (methylethyl ketone) | 2.0 |
| Protective Coating Composition | |
| Component | Amount |
| Polystyrene (LUXTREX ® HF555) | 20 grams |
| Dichloromethane | 1 liter |
| Primer Coating Composition | |
| Component | Amount |
| Polystyrene (LUXTREX ® HF555) | 20 grams |
| Dichloromethane | 1 liter |

One liter of dichloromethane was placed in a suitable mixing vat, 20 grams of polystyrene in pellet form was added slowly to the solvent and stirring continued until all of the styrene had dissolved. The composition so formed was used both as the primer composition and protective coating composition.

The primer composition was placed in a reservoir of an industrial spray gun. A substrate, in this case the roof of a building, was then coated in strips with the primer composition.

The bird repellant composition as described above was prepared as a gel for utilization in a cartridge delivery form. A bead of the bird repellant gel was laid down upon a section of the substrate. The gel was permitted to dry for approximately 1.5 hours.

The protective coating composition prepared as described above was placed in a reservoir of an industrial spray gun. The protective coating layer was then sprayed over the surface of the bird repellant gel. A surface coating of approximately 0.5 millimeter thick of the polystyrene was thus formed. The coating took approximately two hours to fully dry.

The protected bird repellant gel was then monitored for three days at which time it was noted that birds landing on the surface easily broke through the protective layer and were repelled by the tackiness of the bird repellant gel. However, the birds did not become adhered to the roof by the gel.

In areas where there had not been contact with birds, deterioration due to build-up of dust, leaves and the like upon the surface of the bead was substantially diminished.

At the end of five days, attempts were made to remove the bird repellant bead as prepared in Example 1 and Example 2. The bead was easily removed from the sample bearing the primer layer. However, the bead was extremely difficult to remove from the substrate which did not bear the primer layer.

EXAMPLE 3

Two sintered glass crucibles (porosity number 1) were coated with the bird repellant coating prepared according to Example 1 above where one crucible was precoated with a primer coating composition prepared according to Example 2 above (see Figures a and 2). FIG. 1 is a side view of a sintered glass crucible with a bird repellant coating according to the present invention applied to its upper surface.

FIG. 2 is a bottom view of two sintered glass crucibles coated as in FIG. 1. The sintered glass crucible on the left does not have an initial protective coating layer and shows considerable darkening where the bird repellant gel has come through.

A vacuum was applied to the surface away from the bird repellant gel to both crucibles.

The coating proved to be an effective barrier to the bird repellant gel and did not allow it to pass through the porous surface even under a strong vacuum (10–15 mm Hg). It can be concluded that the surface coating does not allow the bird repellant gel to be absorbed into porous materials.

What is claimed is:

1. A multi-layer bird repellant coating composition for a substrate comprising:

(i) at least one bird repellant bead or strip formed from a bird repellant gel composition including:

(a) about 75 to 98% by weight based on the total weight of the gel composition of a high molecular weight polybutene having a molecular weight of 1300 to 1500 and a low molecular weight polybutene having a molecular weight of 900 to 1000;

(b) about 1 to 7% by weight based on the total weight of the gel composition of a clay-based thickening agent; and (c) about 1 to 3% by weight based on the total weight of the gel composition of a polar organic solvent swelling agent;

said bird repellant bead or strip having sufficient tackiness to repel birds but not to substantially retard the birds and having sufficient viscosity to minimize the flattening of said bead or strip; and (ii) a protective coating layer on said bird repellant bead or strip, said protective coating layer formed by application to the bead or strip of a coating composition comprising:

(a) an effective amount of a polymeric component, which polymeric component includes at least one vinyl aromatic polymer or vinyl aromatic copolymer, (b) an effective amount of a solvent or emulsifier for the polymeric component;

the protective coating layer being sufficient brittle that the surface thereof is broken, in use, on contact with a bird.

2. The multi-layer bird repellant coating composition of claim 1 wherein the clay-based thickening agent of the bird repellant gel component is a hydrophobic, organophilic clay containing montmorillonite and aluminum hydrosilicate particles bonded to fatty quaternary ammonium ions.

3. The multi-layer bird repellant coating composition of claim 2 wherein the swelling agent of the bird repellant gel composition is selected from the group consisting of methanol, acetone, methylethyl ketone and mixtures thereof.

4. The multi-layer repellant coating composition according of claim 1 wherein the polymeric component (ii) of the protective coating composition is present in an amount of approximately 2 to 40% weight per volume based on the volume of emulsifier or solvent in the protective coating composition.

5. The multi-layer bird repellant coating composition according to claim 4 wherein the protective coating composition includes a styrene polymer or styrene copolymer and a solvent selected from dichloromethane, toluene, ethylacetate, tetrahydrofuran, cyclohexane, benzene, dioxane, methylethylketone, butyl acetate and lower chlorinated aliphatic hydrocarbons.

6. A multi-layer bird repellant coating composition according to claim 1 further comprising:

(iii) a primer layer, below the at least one bird repellant bead or strip (i), formed from a primer coating composition comprising:

(a) an effective amount of a polymeric primer component which primer component includes at least one vinyl aromatic polymer; and (b) an effective solvent or emulsifier for the polymeric primer component.

7. A method for repelling birds from a substrate, which method includes (i) coating at least a portion of the substrate, in turn, with (a) at least one bird repellant bead or strip formed from a bird repellant gel composition including about 75 to 98% by weight based on the total weight of the gel composition of a high molecular weight polybutene having a molecular weight of 1300 to 1500 and a low molecular weight polybutene having a molecular weight of 900 to 1000; about 1 to 7% by weight based on the total weight of the gel composition of a clay-based thickening agent; and about 1 to 3% by weight based on the total weight of the gel composition of a polar organic solvent swelling agent; and (b) a protective coating layer formed from an effective amount of a protective coating composition comprising a polymeric component, which polymeric component includes at least one vinyl aromatic polymer or vinyl aromatic copolymer, and an effective amount of a solvent or emulsifier for the polymeric component.

8. The method according to claim 7 further comprising:

(ii) drying the at least one bird repellant bead or strip prior to coating it with the protective coating layer.

9. The method according to claim 8 further comprising, prior to step (i), the preliminary step of coating the substrate with a primer coating layer formed from a primer coating composition which includes an effective amount of a polymeric primer component which primer component includes at least one vinyl aromatic polymer, and an effective solvent or emulsifier for the polymeric primer component.

* * * * *

UNITED STATES PATENT AND TRADEMARK OFFICE
CERTIFICATE OF CORRECTION

PATENT NO. : 4,873,082

DATED : October 10, 1989

INVENTOR(S) : Paul Cacioli and Roger Snow

It is certified that error appears in the above-identified patent and that said Letters Patent is hereby corrected as shown below:

ON TITLE PAGE: [63] Related U.S. Applications, line 2, "Jun. 14" should read --June 15--.

At Col. 3, line 27, "(9181)" should read --(1981)--.

At Col. 3, line 59, "25" should read --2%--.

At Col. 5, line 4, "on" should read --one--.

At Col. 6, line 27, "tool" should read --took--.

At Col. 7, line 35, "Fig a" should read --Fig. 1--.

At Col. 8, line 15, "sufficient" should read --sufficiently--.

Signed and Sealed this

Fifth Day of November, 1991

Attest:

HARRY F. MANBECK, JR.

*Attesting Officer*     *Commissioner of Patents and Trademarks*